US007553483B2

(12) United States Patent
Proudfoot et al.

(10) Patent No.: US 7,553,483 B2

(45) Date of Patent: Jun. 30, 2009

(54) CHEMOKINE MUTANTS ACTING AS CHEMOKINE ANTAGONISTS

(75) Inventors: Amanda Proudfoot, Chens sur Leman (FR); Marie Kosco-Vilbois, Minzier (FR); Jeffrey Shaw, Geneva (CH)

(73) Assignee: Merck Serono SA, Coinsins, Vaud (CH)

(*) Notice: Subject to any disclaimer, the term of this patent is extended or adjusted under 35 U.S.C. 154(b) by 433 days.

(21) Appl. No.: 10/499,100

(22) PCT Filed: Dec. 16, 2002

(86) PCT No.: PCT/EP02/14325

§ 371 (c)(1), (2), (4) Date: Feb. 18, 2005

(87) PCT Pub. No.: WO03/051921

PCT Pub. Date: Jun. 26, 2003

(65) Prior Publication Data

US 2005/0220757 A1 Oct. 6, 2005

(30) Foreign Application Priority Data

Dec. 17, 2001 (EP) .................................. 01000761

(51) Int. Cl.
*A61K 45/00* (2006.01)
*A61K 39/00* (2006.01)

(52) U.S. Cl. ................. 424/85.1; 424/185.1; 424/198.1

(58) Field of Classification Search ....................... None
See application file for complete search history.

(56) References Cited

U.S. PATENT DOCUMENTS

| | | | |
|---|---|---|---|
| 6,057,123 | A | 5/2000 | Craig et al. |
| 6,159,711 | A | 12/2000 | Proudfoot et al. |

FOREIGN PATENT DOCUMENTS

| | | | |
|---|---|---|---|
| AU | 5137698 | | 6/1998 |
| EP | 0949271 | | 10/1999 |
| JP | 11243960 | | 9/1999 |
| WO | WO 96/17935 | | 6/1996 |
| WO | WO98/24908 | * | 6/1998 |
| WO | WO 98/24908 | | 6/1998 |
| WO | WO 99/16877 | | 4/1999 |
| WO | WO 99/33989 | | 7/1999 |
| WO | WO00/04926 | * | 2/2000 |
| WO | WO00/78334 | * | 12/2000 |
| WO | WO 02/28419 | | 4/2002 |

OTHER PUBLICATIONS

Appay, V. et al. "RANTES: a Versatile and Controversial Chemokine" *Trends in Immunology*, Feb. 2001, pp. 83-87, vol. 22, No. 2.

Beck, C. G. et al. "The Viral CC Chemokine-binding Protein vCCI Inhibits Monocyte Chemoattractant Protein-1 Activity by Masking Its CCR2B-binding Site" *The Journal of Biological Chemistry*, Nov. 16, 2001, pp. 43270-43276, vol. 276, No. 46.

Gong, J. H. et al. "Antagonists of Monocyte Chemoattractant Protein 1 Identified by Modification of Functionally Critical $NH_2$-terminal Residues" *J. Exp. Med.*, Feb. 1995, pp. 631-640, vol. 181.

Gong, J. H. et al. "Rantes and MCP-3 Antagonists Bind Multiple Chemokine Receptors" *The Journal of Biological Chemistry*, May 3, 1996, pp. 10521-10527, vol. 271, No. 18.

Hemmerich, S. et al. "Identification of Residues in the Monocyte Chemotactic Protein-1 That Contact the MCP-1 Receptor, CCR2" *Biochemistry*, Sep. 15, 1999, pp. 13013-13025, vol. 38.

Martin, L. et al. "Structural and Functional Analysis of the RANTES-Glycosaminoglycans Interactions" *Biochemistry*, May 4, 2001, pp. 6303-6318, vol. 40.

Nardese, V. et al. "Structural Determinants of CCR5 Recognition and HIV-1 Blockade in RANTES" *Nature Structural Biology*, Jul. 2001, pp. 611-615, vol. 8, No. 7.

http://www.psc.edu/biomed/genedoc/gdsim.htm, "Similarity Tables: GeneDoc's Similarity Tables", Nov. 17, 2006, pp. 1-6.

* cited by examiner

*Primary Examiner*—Robert Landsman
*Assistant Examiner*—Bruce D Hissong
(74) *Attorney, Agent, or Firm*—Saliwanchik, Lloyd & Saliwanchik

(57) ABSTRACT

Mutants of specific CC-chemokines containing a non-conservative substitution in a conserved consensus sequence act as CC-chemokine antagonists, and can be effectively used in the treatment of autoimmune and inflammatory diseases, cancers, and viral or bacterial infections. Particularly preferred are the RANTES/CCL5 mutants having the amino acid sequence of SEQ ID NO: 1, 2, 3, or 4.

20 Claims, 9 Drawing Sheets

Figure 1

```
   ATG AAA AAA AAA TGG CCG CGT TCC CCA TAT TCC TCG GAC ACC ACA CCC TGC
 1  M   K   K   K   W   P   R   S   P   Y   S   S   D   T   T   P   C  10

   TGC TTT GCC TAC ATT GCC CGC CCA CTG CCC CGT GCC CAC ATC AAG GAG TAT
11  C   F   A   Y   I   A   R   P   L   P   R   A   H   I   K   E   Y  27

   TTC TAC ACC AGT AAC AAG TGC TCC AAC CCA GCA GTC GTC TTT GTC ACC CGA
28  F   Y   T   S   N   K   C   S   N   P   A   V   V   F   V   T   R  44

   AAG AAC CGC CAA GTG TGT GCC AAC CCA GAG AAG AAA TGG GTT CGG GAG TAC
45  K   N   R   Q   V   C   A   N   P   E   K   K   W   V   R   E   Y  61

   ATC AAC TCT TTG GAG ATG AGC
62  I   N   S   L   E   M   S  68
```

Figure 9

| | | Xa | Xb | |
|---|---|---|---|---|
| CCL1 | CCFSFAEQEIPLRAILCYR_N | TS | S | IC |
| CCL2 | CCYNFTNRKISVQRLASYRRI | TS | S | KC |
| CCL3 | CCFSYTSRQIPQNFIADYF_E | TS | S | QC |
| CCL4 | CCFSYTARKLPRNFVVDYY_E | TS | S | LC |
| CCL5 | CCFAYIARPLPRAHIKEYF_Y | TS | G | KC |
| CCL7 | CCYRFINKKIPKQRLESYRRT | TS | S | HC |
| CCL11 | CCFNLANRKIPLQRLESYRRI | TS | G | KC |
| CCL13 | CCFTFSSKKISLQRLKSYV_I | TT | S | RC |
| CCL15 | CCTSYISQSIPCSLMKSYF_E | TS | S | EC |

SEQUENCE LISTING

```
<160> NUMBER OF SEQ ID NOS: 13

<210> SEQ ID NO 1
<211> LENGTH: 68
<212> TYPE: PRT
<213> ORGANISM: Artificial sequence
<220> FEATURE:
<223> OTHER INFORMATION: mutant chemokine

<400> SEQUENCE: 1

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Asn
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65


<210> SEQ ID NO 2
<211> LENGTH: 68
<212> TYPE: PRT
<213> ORGANISM: Artificial sequence
<220> FEATURE:
<223> OTHER INFORMATION: mutant chemokine

<400> SEQUENCE: 2

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Pro
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65


<210> SEQ ID NO 3
<211> LENGTH: 68
<212> TYPE: PRT
<213> ORGANISM: Artificial sequence
<220> FEATURE:
<223> OTHER INFORMATION: mutant chemokine

<400> SEQUENCE: 3

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Asp
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65
```

-continued

<210> SEQ ID NO 4
<211> LENGTH: 68
<212> TYPE: PRT
<213> ORGANISM: Artificial sequence
<220> FEATURE:
<223> OTHER INFORMATION: mutant chemokine

<400> SEQUENCE: 4

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Lys
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65
```

<210> SEQ ID NO 5
<211> LENGTH: 69
<212> TYPE: PRT
<213> ORGANISM: Artificial Sequence
<220> FEATURE:
<223> OTHER INFORMATION: mutant chemokine
<220> FEATURE:
<221> NAME/KEY: mat_peptide
<222> LOCATION: (1)..(46)

<400> SEQUENCE: 5

```
Met Ser Pro Tyr Ser Ser Asp Thr Thr Pro Cys Cys Phe Ala Tyr Ile
            -20                 -15                 -10

Ala Arg Pro Leu Pro Arg Ala His Ile Lys Glu Tyr Phe Tyr Thr Ser
        -5              -1  1               5

Asn Lys Cys Ser Asn Pro Ala Val Val Phe Val Thr Arg Lys Asn Arg
10                  15                  20                  25

Gln Val Cys Ala Asn Pro Glu Lys Lys Trp Val Arg Glu Tyr Ile Asn
                30                  35                  40

Ser Leu Glu Met Ser
            45
```

<210> SEQ ID NO 6
<211> LENGTH: 66
<212> TYPE: PRT
<213> ORGANISM: Artificial sequence
<220> FEATURE:
<223> OTHER INFORMATION: mutant chemokine
<220> FEATURE:
<221> NAME/KEY: mat_peptide
<222> LOCATION: (1)..(43)

<400> SEQUENCE: 6

```
Tyr Ser Ser Asp Thr Thr Pro Cys Cys Phe Ala Tyr Ile Ala Arg Pro
            -20                 -15                 -10

Leu Pro Arg Ala His Ile Lys Glu Tyr Phe Tyr Thr Ser Asn Lys Cys
        -5              -1  1               5

Ser Asn Pro Ala Val Val Phe Val Thr Arg Lys Asn Arg Gln Val Cys
10                  15                  20                  25

Ala Asn Pro Glu Lys Lys Trp Val Arg Glu Tyr Ile Asn Ser Leu Glu
                30                  35                  40

Met Ser
```

-continued

<210> SEQ ID NO 7
<211> LENGTH: 68
<212> TYPE: PRT
<213> ORGANISM: Artificial sequence
<220> FEATURE:
<223> OTHER INFORMATION: mutant chemokine

<400> SEQUENCE: 7

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Asn
            20                  25                  30

Lys Cys Ser Asn Pro Ala Val Val Phe Val Thr Ala Ala Asn Ala Gln
        35                  40                  45

Val Cys Ala Asn Pro Glu Lys Lys Trp Val Arg Glu Tyr Ile Asn Ser
    50                  55                  60

Leu Glu Met Ser
65
```

<210> SEQ ID NO 8
<211> LENGTH: 225
<212> TYPE: DNA
<213> ORGANISM: Artificial sequence
<220> FEATURE:
<223> OTHER INFORMATION: mutant chemokine

<400> SEQUENCE: 8

```
atgaaaaaaa aatggccgcg ttccccatat tcctcggaca ccacaccctg ctgctttgcc      60

tacattgccc gcccactgcc ccgtgcccac atcaaggagt atttctacac cagtaacaag     120

tgctccaacc cagcagtcgt ctttgtcacc cgaaagaacc gccaagtgtg tgccaaccca     180

gagaagaaat gggttcggga gtacatcaac tctttggaga tgagc                     225
```

<210> SEQ ID NO 9
<211> LENGTH: 75
<212> TYPE: PRT
<213> ORGANISM: Artificial sequence
<220> FEATURE:
<223> OTHER INFORMATION: mutant chemokine

<400> SEQUENCE: 9

```
Met Lys Lys Lys Trp Pro Arg Ser Pro Tyr Ser Ser Asp Thr Thr Pro
1               5                   10                  15

Cys Cys Phe Ala Tyr Ile Ala Arg Pro Leu Pro Arg Ala His Ile Lys
            20                  25                  30

Glu Tyr Phe Tyr Thr Ser Asn Lys Cys Ser Asn Pro Ala Val Val Phe
        35                  40                  45

Val Thr Arg Lys Asn Arg Gln Val Cys Ala Asn Pro Glu Lys Lys Trp
    50                  55                  60

Val Arg Glu Tyr Ile Asn Ser Leu Glu Met Ser
65                  70                  75
```

<210> SEQ ID NO 10
<211> LENGTH: 48
<212> TYPE: DNA
<213> ORGANISM: Artificial sequence
<220> FEATURE:
<223> OTHER INFORMATION: mutant chemokine

<400> SEQUENCE: 10

-continued

```
atcgtcatga aaaaaaaatg gccgcgttcc ccatattcct cggacacc            48


<210> SEQ ID NO 11
<211> LENGTH: 33
<212> TYPE: DNA
<213> ORGANISM: Artificial sequence
<220> FEATURE:
<223> OTHER INFORMATION: mutant chemokine

<400> SEQUENCE: 11

tgggttggag cacttgttac tggtgtagaa ata                            33


<210> SEQ ID NO 12
<211> LENGTH: 33
<212> TYPE: DNA
<213> ORGANISM: Artificial sequence
<220> FEATURE:
<223> OTHER INFORMATION: mutant chemokine

<400> SEQUENCE: 12

tatttctaca ccagtaacaa gtgctccaac cca                            33


<210> SEQ ID NO 13
<211> LENGTH: 34
<212> TYPE: DNA
<213> ORGANISM: Artificial sequence
<220> FEATURE:
<223> OTHER INFORMATION: mutant chemokine

<400> SEQUENCE: 13

atgcctcgag ctagctcatc tccaaagagt tgat                           34
```

CHEMOKINE MUTANTS ACTING AS CHEMOKINE ANTAGONISTS

CROSS-REFERENCE TO RELATED APPLICATION

This application is the U.S. national stage application of International Patent Application No. PCT/EP02/14325, filed Dec. 16, 2002, which claims priority to European Patent Application Number 01000761.5, filed Dec. 17, 2001.

FIELD OF THE INVENTION

The present invention relates to novel CC-chemokine mutants acting as CC-chemokine antagonists.

BACKGROUND OF THE INVENTION

Chemokines are secreted pro-inflammatory proteins of small dimensions (70-130 amino acids) mostly involved in the directional migration and activation of cells, especially the extravasation of leukocytes from the blood to tissue localizations needing the recruitment of these cells (Baggiolini M et al., 1997; Rossi D and Zlotnik A, 2000; Fernandez E J and Lolis E, 2002). Usually chemokines are produced at the site of an injury, inflammation, or other tissue alteration in a paracrine or autocrine fashion, triggering cell-type specific migration and activation.

Depending on the number and the position of the conserved cysteines in the sequence, chemokines are classified into C, CC, CXC and $CX_3C$ chemokines. Inside each of these families, chemokines can be further grouped according to the homology of the entire sequence, or of specific segments.

A series of heptahelical G-protein coupled membrane receptors, are the binding partners that allow chemokines to exert their biological activity on the target cells, which present specific combinations of receptors according to their state and/or type. An unified nomenclature for chemokine ligands and receptors, which were originally named by the scientists discovering them in a very heterogeneous manner, has been proposed to associate each of these molecule to a systemic name including a progressive number: CCL1 CCL2, etc. for CC chemokines; CCR1 CCR2, etc. for CC chemokines receptors, and so on.

The physiological effects of chemokines result from a complex and integrated system of concurrent interactions. The receptors often have overlapping ligand specificity, so that a single receptor can bind different chemokines, as well a single chemokine can bind different receptors. In particular, N-terminal domain of chemokines is involved in receptor binding and N-terminal processing can either activate chemokines or render chemokines completely inactive.

Even though there are potential drawbacks in using chemokines as therapeutic agents (tendency to aggregate, promiscuous binding), these molecules offer the possibility for therapeutic intervention in pathological conditions associated to such processes, in particular by inhibiting/antagonizing specific chemokines and their receptors at the scope to preventing the excessive recruitment and activation of cells, in particular leukocytes, for a variety of indications related to inflammatory and autoimmune diseases, cancers, and bacterial or viral infections (Carter P H, 2002; Schneider G P et al., 2001, Baggiolini M, 2001; Godessart N and Kunkel S L, 2001; Proudfoot A et al., 2000).

Amongst all the chemokines characterized so far, CC-chemokines, such as CCL5 (also known as RANTES; Appay V and Rowland-Jones S L, 2001) have been intensively studied to identify therapeutically useful molecules. Variants of CC-chemokines, missing up to nine N-terminal amino acids, have been tested for their activity as inhibitors or antagonists of the naturally occurring forms. These molecules are inactive on monocytes and are useful as receptor antagonists (Gong J and Clark-Lewis I, 1995; Gong J H et al., 1996; WO 99/16877). Alternatively, N-terminal extension of the mature CC-chemokine with one Methionine results in almost complete inactivation of the molecule, which also behaves as an antagonist for the authentic one (WO 96/17935).

Moreover, in order to perform structure-function analysis of CC-chemokines, variants containing substitutions or chemical modifications in different positions, as well as CC-chemokine derived peptides, have been tested for the interactions with receptors or other molecules, such as Glycosaminoglycans (GAGs). Some of these variants have been disclosed as having significatively altered binding properties, and sometimes they are active as CC-chemokine antagonists, having potential therapeutic applications in the treatment of HIV infection and inflammatory or allergic diseases (WO 99/33989; U.S. Pat. No. 6,057,123; PCT/EP01/11428; Nardese V et al., 2001; Martin L et al., 2001; Beck C et al., 2001; Hemmerich S et al., 1999).

However, none of these approaches have exhaustively studied the properties of all mutants deriving from the non-conservative substitutions in each single positions conserved in CC-chemokines, or in a subset of them.

SUMMARY OF THE INVENTION

It has been surprisingly found that specific mutants of a CC-chemokine (CCL5, also known as RANTES), containing a single non-conservative substitution in a consensus sequence common to a subset of CC-chemokines, act as antagonist of this CC-chemokine.

These evidences can be exploited to generate mutants having similar properties for this subset of CC-chemokines sharing the same consensus sequence. Molecules prepared in accordance with the present invention can be used in the treatment of inflammatory and autoimmune diseases, cancers, and bacterial or viral infections.

Other features and advantages of the invention will be apparent from the following detailed description.

DESCRIPTION OF THE FIGURES

FIG. 1: DNA and protein sequence (SEQ ID NO: 8 and 9, respectively) of secRANTES G32N. The mature sequence of RANTES G32N (SEQ ID NO: 1; underlined) is obtained after digesting the *E. coli*-expressed secRANTES G32N with trypsin, eliminating leader sequence MKKKWPR. The specific position (called position Xb in FIG. 9 and claim 1) which is mutated in RANTES G32N and in the other corresponding mutants RANTES G32P (SEQ ID NO: 2), RANTES G32D (SEQ ID NO: 3), RANTES G32K (SEQ ID NO: 4), Met-RANTES G32N (SEQ ID NO: 5), RANTES (3-68) G32N (SEQ ID NO: 6), and RANTES G32N ALL40'S (SEQ ID NO: 7), is boxed. The numbering is indicated with reference to the mature sequence of RANTES.

FIG. 9: sequence alignment of the amino acid sequences of CC chemokines containing the consensus sequence defined in the present invention: human CC-chemokine CCL1 (also known as I-309, SWISSPROT acc. no. P22362; amino acids 33-57 of SEQ ID NO: 14), CCL2 (also known as MCP-1, SWISSPROT acc. no. P13500; amino acids 34-59 of SEQ ID NO: 15), CCL3 (also known as MIP-1alpha; SWISSPROT acc. no. P10147; amino acids 33-57 of SEQ ID NO: 16), CCL4 (also known as MIP-1beta; SWISSPROT acc. no. P13326; amino acids 34-58 of SEQ ID NO: 17), CCL5 (also known as RANTES, SWISSPROT acc. no. P13501; amino acids 33-57 of SEQ ID NO: 18), CCL7 (also known as MCP-3, SWISSPROT acc. no. P80098; amino acids 34-59 of SEQ ID NO: 19), CCL11 (also known as Eotaxin, SWISSPROT acc. no. P51671; amino acids 32-57 of SEQ ID NO: 20), CCL13 (also known as MCP-4, SWISSPROT acc. no. Q99616; amino acids 34-58 of SEQ ID NO: 21), and CCL15 (also known as HCC-2, SWISSPROT acc. no. Q16663; amino acids 53-77 of SEQ ID NO: 22). The corresponding residues $X_a$ are boxed and the corresponding position $X_b$ to be substituted in a non-conservative manner is underlined.

DETAILED DESCRIPTION OF THE INVENTION

Figure 2A:
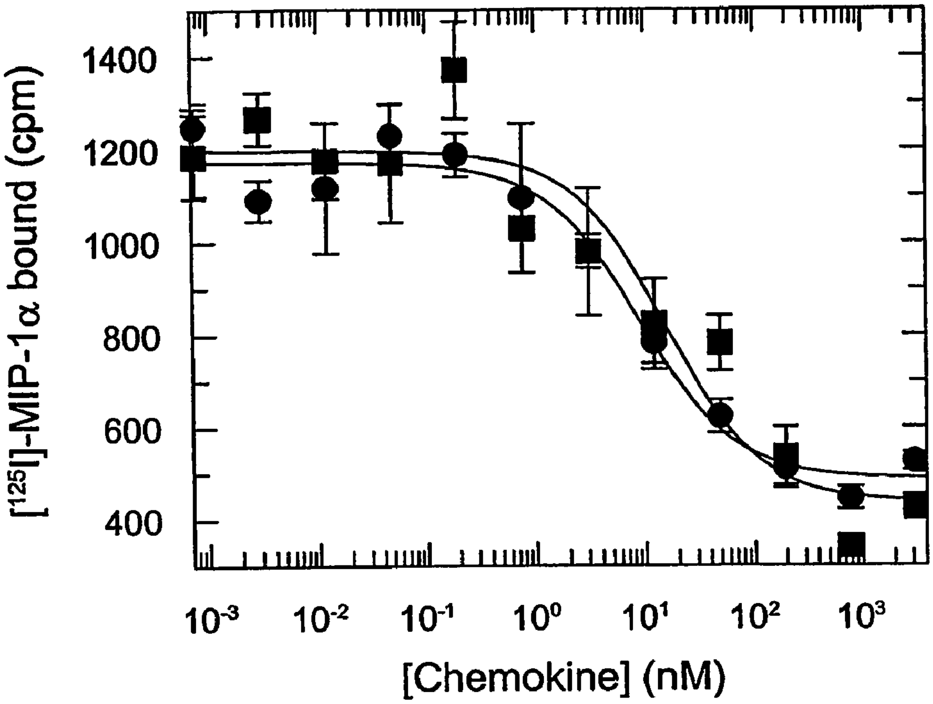
FIG. 2: equilibrium competition receptor binding assays. Displacement of [$^{125}$I]-MIP-1α by RANTES (■) or RANTES G32A (●) from (a) CCR1 and (b) CCR5.

On the basis of crystallographic studies, we have now found that by mutating RANTES (CCL5) at position 32 it is possible to obtain a RANTES antagonist, useful in the treatment of inflammatory and autoimmune diseases, cancers, and bacterial or viral infections. The analysis of the structure of RANTES G32N and comparison with the structure and the sequence of other known CC chemokines more similar to CCL5 in that region (see FIG. 9) suggests that this residue plays a general role in biological activity of a subset of CC-chemokines.

Therefore we have defined a consensus sequence in the segment comprised between the Cys-Cys site characterizing CC-chemokines and the next conserved Cys residues (FIG. 9) which is common to a subset of CC-chemokines, and which contains a conserved residue that, if appropriately substituted, transforms the CC-chemokine into a CC-chemokine antagonist. Prior art fails to provide any indication on the importance and the possible use of a non-conservative substitution in this position and in this particular group of CC-chemokines defined on such consensus sequence (WO 99/33989; U.S. Pat. No. 6,057,123; PCT/EP01/11428; Nardese V et al., 2001; Mayer M R and Stone M J, 2001; Martin L et al., 2001; Beck C et al., 2001; Hemmerich S et al., 1999).

Therefore the main object of the present invention is to provide mutants of a CC-chemokine containing the following consensus sequence:

$$C\text{-}C\text{-}(X)_{18\text{-}19}\text{-}(X_a)_2\text{-}X_b\text{-}X\text{-}C$$

wherein:

C stands for Cysteine;

X stands for any amino acid;

$X_a$ stands for Serine or Threonine;

$X_b$ stands for Glycine or Serine;

and wherein said mutant:

a) contains a non-conservative substitution in the position $X_b$; and b) acts as an antagonist of the corresponding CC-chemokine Human CC-chemokines sharing such a consensus sequence are CCL1, CCL2, CCL3, CCL4, CCL5, CCL7, CCL11, CCL13, and CCL15.

The amino acid in the position Xb can be substituted in a non-conservative manner by any other amino acid having properties different from the ones of Glycine and Serine (small, neutral, and flexible). Preferably, the substitution involves larger, polar, and/or rigid amino acids such as, Proline, Lysine, Arginine, Histidine, Aspartic acid, Glutamic Acid, Glutamine, or Asparagine. Examples of such mutants are provided for RANTES/CCL5 in the present patent application (SEQ ID NO: 1, 2, 3, and 4).

In addition to the mutation at position Xb, the mutants of the present invention can include other modifications with respect to the wild-type molecule, such as deletions, substitutions, or additions, generating active mutants of the above defined CC-chemokine antagonists. These additional modifications should be intended to maintain, or even potentiate, the antagonistic properties of the mutants exemplified In the present patent application. This category of molecules includes natural or artificial analogs of said sequence, wherein one or more amino acid residues have been added, deleted, or substituted, provided they display the same biological activity characterized in the present invention, or by any other relevant means known in the art, at comparable or higher levels.

Specific CC-chemokine mutants may have one or more amino acids being added, deleted, or substituted in the N-terminal region known to affect receptor binding. Such additional mutations can be already known to produce CC-chemokine antagonists. For example, the RANTES mutants of the present invention can also contain an additional N-terminus amino acid, as described in WO 96/17935 or can lack the first two N-terminal amino acids as described in WO 99/16877. Accordingly, molecules, based on RANTES G32N and having an amino acid sequence of Met-RANTES G32N (SEQ ID NO: 5) and RANTES (3-68) G32N (SEQ ID NO: 6), may be obtained and these are also covered by the present invention.

Alternativly, RANTES G32N can also contain single mutations in other sites, as described in WO 99/33989, or can contain other mutations in the GAG-binding domain as described in PCT/EP01/11428. In this latter case, the molecule has an amino acid sequence of RANTES G32N ALL40'S (SEQ ID NO: 7).

These polypeptides can be prepared by chemical synthesis, by site-directed mutagenesis techniques, or any other known technique suitable thereof, which provide a finite set of substantially corresponding mutated or shortened peptides or polypeptides which can be routinely obtained and tested by one of ordinary skill in the art using the teachings presented in the prior art and in the Examples of the present patent application. Similar compounds may also result from conventional mutagenesis technique of the encoding DNA, from combinatorial technologies at the level of encoding DNA sequence (such as DNA shuffling, phage display/selection), or from computer-aided design studies for designing decoy for chemokine interactions (Rajarathnam K, 2002).

In accordance with the present invention, other additional preferred changes in these active mutants are commonly known as "conservative" or "safe" substitutions, that is, with amino acids having sufficiently similar chemical properties, in order to maintain the structure and the biological function of the molecule as CC-chemokine antagonist. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provide many models on which the selection of conservative amino acids substitutions can be performed on the basis of statistical and physico-chemical studies on the sequence and/or the structure of natural protein (Rogov S I and Nekrasov A N, 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L R et al., 2000). The synonymous amino acid groups and more preferred synonymous groups are those defined in Table I.

Peptides corresponding to subsequences belonging to CC-chemokines have been disclosed in the prior art (Nardese V et al., 2001). Similar peptides, comprised in any of the previously identified subset of CC-chemokines and containing a non-conservative substitution of the residue in the position corresponding to the position $X_b$ previously indicated in the consensus sequence, also form part of the present invention. These peptides should correspond to subsequences belonging to the previously Indicated CC-chemokines, should be made of at least 5 amino acids, but preferably of 10 or more amino acids.

Moreover, alternative antagonists based on such peptides can be generated in the form of peptide mimetics (also called peptidomimetics), in which the nature of peptide or polypeptide has been chemically modified at the level of amino acid side chains, of amino acid chirality, and/or of the peptide backbone. These alterations are intended to provide antagonists with improved preparation, potency and/or pharmacokinetics features.

For example, when the peptide is susceptible to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl. Many other modifications providing increased potency, prolonged activity, easiness of purification, and/or increased half-life have been described in the literature (WO 02/10195; Villain M et al., 2001).

Preferred alternative, "synonymous" groups for amino acids derivatives included in peptide mimetics are those defined in Table II. A non-exhaustive list of amino acid derivatives also include amino-isobutyric acid (Aib), hydroxy-proline (Hyp), 1,2,3,4-tetrahydro-isoquinoline-3-COOH, indoline-2-carboxylic acid, 4-difluoro-proline, L-thiazolidine-4-carboxylic acid, L-homoproline, 3,4-dehydro-proline, 3,4-dihydroxy-phenylalanine, cyclohexyl-glycine, and phenyl-glycine.

By "amino acid derivative" is intended an amino acid or amino acid-like chemical entity other than one of the 20 genetically encoded naturally occurring amino acids. In particular, the amino acid derivative may contain substituted or non-substituted alkyl linear, branched, or cyclic moieties, and may include one or more heteroatoms. The amino acid derivatives can be made de novo or obtained from commercial sources (Calbiochem-Novabiochem AG, Switzerland; Bachem, USA).

Various methodologies for incorporating unnatural amino acids derivatives into proteins, using both in vitro and in vivo translation systems, to probe and/or improve protein structure and function are disclosed in the literature (Dougherty D A, 2000). Techniques for the synthesis and the development of peptide mimetics, as well as non-peptide mimetics, are also well known in the art (Sawyer T K, 1997; Hruby V J and Balse P M, 2000; Golebiowski A et al., 2001).

The term "CC-chemokine antagonist" means any molecule, which acts as antagonist to the corresponding mature and/or full-length, naturally-occurring (wild-type) CC-chemokine.

The term "active" means that such alternative compounds should maintain the antagonistic properties of the CC-chemokines mutants of the present invention, and should be as well pharmaceutically acceptable and useful.

The present patent application also discloses polypeptides comprising antagonists of CC-chemokines as defined above and an amino acid sequence belonging to a protein sequence other than the corresponding CC-chemokine. This heterologous sequence should provide additional properties without considerably impairing the antagonistic activity. Examples of such additional properties are an easier purification procedure, a longer lasting half-life in body fluids, an additional binding moiety, the maturation by means of an endoproteolytic digestion, or extracellular localization. This latter feature is of particular importance for defining a specific group of fusion or chimeric proteins included in the above definition since it allows the molecules defined as CC-chemokine antagonists in this patent application to be localized in the space where not only where the isolation and purification of these polypeptides is facilitated, but also where CC-chemokines naturally interact with receptors and other molecules. Design of the moieties, ligands, and linkers, as well methods and strategies for the construction, purification, detection and use of fusion proteins are widely discussed in the literature (Nilsson J et al., 1997; "Applications of chimeric genes and hybrid proteins" Methods Enzymol. Vol. 326-328, Academic Press, 2000; WO 01/177137).

Additional protein sequences which can be used to generate the antagonists of the present invention can be chosen amongst extracellular domains of membrane-bound protein, immunoglobulin constant regions, multimerization domains, extracellular proteins, signal peptide-containing proteins, export signal-containing proteins. The choice of one or more of these sequences to be fused to the CC-chemokine mutants of the invention is functional to the specific use and/or preparation method.

The polypeptides and the peptides disclosed in the present patent application can be provided in other alternative forms which can be preferred according to the desired method of use and/or production, for example as active fractions, precursors, salts, derivatives, conjugates or complexes.

The "precursors" are compounds which can be converted into the compounds of present invention by metabolic and enzymatic processing prior or after the administration to the cells or to the organism.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as herein used refers to derivatives which can be prepared from the functional groups present on the lateral chains of the amino acid moieties or on the N-/or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups. Alternatively, the derivatives may contain sugars or phosphates groups linked to the functional groups present on the lateral chains of the amino acid moieties. Such molecules can result from in vivo or in vitro processes which do not normally alter primary sequence, for example chemical derivativization of peptides (acetylation or carboxylation), phosphorylation (introduction of phosphotyrosine, phosphoserine, or phosphothreonine residues) or glycosylation (by exposing the peptide to enzymes which affect glycosylation e.g., mammalian glycosylating or deglycosylating enzymes).

Useful conjugates or complexes of the antagonists of the present invention can be generated, using molecules and methods known in the art for improving the detection of the interaction with other proteins (radioactive or fluorescent labels, biotin), therapeutic efficacy (cytotoxic agents, isotopes), or drug delivery efficacy, such as polyethylene glycol and other natural or synthetic polymers (Pillai O and Panchagnula R, 2001). In the latter case, the antagonists may be produced following a site-directed modification of an appropriate residue, present in the natural sequence or introduced by mutating the natural sequence, at an internal or terminal position. Similar modifications have been already disclosed for chemokines (WO 02/04499; WO 02/04015; Vita C et al., 2002).

Any residue can be used for attachment, provided it has a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment. Also, the side chains of the genetically encoded amino acids can be chemically modified for polymer attachment, or unnatural amino acids with appropriate side chain functional groups can be employed. Polymer attachment may be not only to the side chain of the amino acid naturally occurring in a specific position of the antagonist or to the side chain of a natural or unnatural amino acid that replaces the amino acid naturally occurring in a specific position of the antagonist, but also to a carbohydrate or other moiety that is attached to the side chain of the amino acid at the target position.

Polymers suitable for these purposes are biocompatible, namely, they are non-toxic to biological systems, and many such polymers are known. Such polymers may be hydrophobic or hydrophilic in nature, biodegradable, non-biodegradable, or a combination thereof. These polymers include natural polymers (such as collagen, gelatin, cellulose, hyaluronic acid), as well as synthetic polymers (such as polyesters, polyorthoesters, polyanhydrides). Examples of hydrophobic non-degradable polymers include polydimethyl siloxanes, polyurethanes, polytetrafluoroethylenes, polyethylenes, polyvinyl chlorides, and polymethyl methaerylates. Examples of hydrophilic non-degradable polymers include poly(2-hydroxyethyl methacrylate), polyvinyl alcohol, poly (N-vinyl pyrrolidone), polyalkylenes, polyacrylamide, and copolymers thereof. Preferred polymers comprise as a sequential repeat unit ethylene oxide, such as polyethylene glycol (PEG).

The preferred method of attachment employs a combination of peptide synthesis and chemical ligation. Advantageously, the attachment of a water-soluble polymer will be through a biodegradable linker, especially at the amino-terminal region of a protein. Such modification acts to provide the protein in a precursor (or "pro-drug") form, that, upon degradation of the linker releases the protein without polymer modification.

The antagonists of the invention may be prepared by any well known procedure in the art, including recombinant DNA-related technologies, and chemical synthesis technologies.

Another object of the invention are the DNA molecules comprising the DNA sequences coding for the CC-chemokine mutants of the invention, including nucleotide sequences substantially the same.

"Nucleotide sequences substantially the same" includes all other nucleic acid sequences which, by virtue of the degeneracy of the genetic code, also code for the given amino acid sequences.

The invention also includes expression vectors which comprise the above DNAs, host-cells transformed with such vectors and a process of preparation of such CC-chemokine mutants of the invention, comprising culturing said transformed cells in an appropriate culture media, and collecting the expressed proteins. When the vector expresses the antagonists as a fusion protein with extracellular, export signal, or signal peptide containing proteins, the CC-chemokine antagonists can be secreted in the extracellular space, and can be more easily collected and purified from cultured cells in view of further processing.

Expression of any of the recombinant proteins of the invention as mentioned herein can be effected in Eukaryotic cells (e.g. yeasts, insect or mammalian cells) or Prokaryotic cells, using the appropriate expression vectors. Any method known in the art can be employed.

In particular, mammalian cells, such as human, monkey, mouse, and Chinese hamster ovary (CHO) cells in particular, are preferred because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides). Alternatively, any of the specific protocols for the expression of chemokines in bacterial cells disclosed in the literature can be used (Edgerton M D et al., 2000).

Factors of importance in selecting a particular plasmid or viral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species.

The vectors should allow the expression of the isolated or fusion protein including the antagonist of the invention in the Prokaryotic or Eukaryotic host cell under the control of transcriptional initiation/termination regulatory sequences, which are chosen to be constitutively active or inducible in said cell. After the introduction of the vector(s), the host cells are grown in a selective medium, which selects for the growth of vector-containing cells. Expression of the cloned gene sequence(s) results in the production of the desired proteins. A cell line substantially enriched in such cells can be then isolated to provide a stable cell line.

For Eukaryotic hosts (e.g. yeasts, insect or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection.

These objects of the invention can be achieved by combining the disclosure provided by the present patent application on antagonists of CC-chemokines, with the knowledge of common molecular biology techniques. Many books and reviews provides teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

The CC-chemokine mutants of the invention may be prepared by any other well known procedure in the art, in particular, by the well established chemical synthesis procedures, which can be efficiently applied on these molecule given the short length. Totally synthetic CC-chemokines, also containing additional chemical groups, are disclosed in the literature (Brown A et al., 1996; Vita C et al., 2002).

Examples of chemical synthesis technologies are solid phase synthesis and liquid phase synthesis. As a solid phase synthesis, for example, the amino acid corresponding to the carboxy-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the carboxy-terminus to the amino-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method. Finally, the intact full-length peptides are purified and chemically or enzymatically folded (including the formation of disulphide bridges between cysteines) into the corresponding CC-chemokine mutants of the invention.

Purification of the natural, synthetic or recombinant proteins is carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies, heparin, or any other suitable ligand which can bind the target protein at high efficiency and can be immobilized on a gel matrix contained within a column. Impure preparations containing the proteins are passed through the column. The protein will be bound to the column by means of this ligand while the impurities will pass through. After washing, the protein is eluted from the gel by a change in pH or ionic strength. Alternatively, HPLC (High Performance Liquid Chromatography) can be also used.

The present invention also includes purified preparations of the above described CC-chemokine mutants. Purified preparations, as used herein, refers to the preparations which contain at least 1%, preferably at least 5%, by dry weight of the CC-chemokine mutants of the invention.

Another object of the present invention is the use of the CC-chemokine mutants as above defined as medicaments, in particular as the active ingredients in pharmaceutical compositions (and formulated in combination with pharmaceutically acceptable carriers, excipients, stabilizers, adjuvants, or diluents). Still another object is the use of the CC-chemokine mutants of the inventions to produce a pharmaceutical composition for treating or preventing disorders in which the antagonistic properties of said molecules can provide beneficial effects such as, according to the literature on chemokines, autoimmune and inflammatory diseases, cancers, as well as bacterial and viral infections. A non-limitative list of specific disorders includes arthritis, rheumatoid arthritis (RA), psoriatic arthritis, osteoarthritis, systemic lupus erythematosus (SLE), systemic sclerosis, scleroderma, polymyositis, glomerulonephritis, melanoma, caricinoma, leukaemia, lymphoblastoma, liver fibrosis, skin fibrosis, lung fibrosis, allergic or hypersensitivity diseases, dermatitis, Type IV hypersensitivity also called delayed-type hypersensitivity or DTH, asthma, chronic obstructive pulmonary disease (COPD), inflammatory bowel disease (IBD), Crohn's diseases, ulcerative colitis, multiple sclerosis, septic shock, HIV-infection, transplantation, graft-versus-host disease (GVHD), atherosclerosis.

Another object of the present invention is, therefore, the method for treating or preventing any of the above mentioned diseases by administering an effective amount of the chemokine mutants of the invention together with a pharmaceutically acceptable excipient, and/or with another therapeutic composition which acts synergically or in a coordinated manner with the CC-chemokine mutants of the invention. For example, similar synergistic properties of CC-chemokine antagonists have been demonstrated in combination with cyclosporin (WO 00/16796).

An "effective amount" refers to an amount of the active ingredients that is sufficient to affect the course and the severity of the disease, leading to the reduction or remission of such pathology. The effective amount will depend on the route of administration and the condition of the patient.

A further object of the present invention are the pharmaceutical compositions containing the chemokine mutants of the invention, in the presence of one or more pharmaceutically acceptable excipients, for treating or preventing any of the above mentioned diseases. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

"Pharmaceutically acceptable" is meant to encompass any carrier, which does not interfere with the effectiveness of the biological activity of the active ingredient and that is not toxic to the host to which is administered. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil). For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilizers, excipients, buffers and preservatives which may facilitate the processing of the active compounds into preparations which can be used pharmaceutically. Moreover, these compositions may contain another active ingredient which can act synergically or in a coordinated manner with the CC-chemokine mutants of the invention. For example, similar synergistic properties of CC-chemokine antagonists have been demonstrated in combination with cyclosporin (WO 00/16796).

The administration of such active ingredient may be by intravenous, intramuscular or subcutaneous route. Other routes of administration, which may establish the desired blood levels of the respective ingredients, are comprised by the present invention. For example, administration may be by various parenteral routes such as subcutaneous, intravenous, intradermal, intramuscular, intraperitoneal, intranasal, transdermal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

The optimal dose of active ingredient may be appropriately selected according to the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

Usually a daily dosage of active ingredient can be about 0.01 to 100 milligrams per kilogram of body weight. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

Construction and Expression of RANTES Mutants in Position 32

Human RANTES was expressed in *E. coli* in four mutated forms in position 32, which either Gly or Ser in a subset of CC-chemokines which have either Ser or Thr in the two immediately preceding positions (compare FIGS. 1 and 10).

The RANTES mutants were expressed as mature RANTES variants containing a heterologous Met-starting, leader sequence (MKKKWPR), which is later eliminated from this precursor (secRANTES G32N protein; SEQ ID NO: 9; FIG. 1) using a proteolytic enzyme to obtain the mature protein (RANTES G32N; SEQ ID NO: 1). The mutated position is indicated as 32 since it refers to the mature protein.

The DNA encoding for the mutant (secRANTES G32N DNA; SEQ ID NO: 8; FIG. 1) was generated by PCR mutagenesis of human RANTES by performing a two-step PCR-based mutagenesis, using two oligonucleotides pairs hybridizing a human RANTES sequence fused to the same leader sequence and cloned in the expression vector pET24d (Novagen).

The 5' end portion of secRANTES G32N DNA was generated using, as forward primer, a primer including the leader sequence and 5' sequence of the mature human RANTES (primer P1; SEQ ID NO: 10) and, as reverse primer, a mutagenic primer for substituting a Gly codon with an Asn codon by changing two nucleotides (primer P2; SEQ ID NO: 11). The 3' end portion of secRANTES G32N DNA was generated using, as forward primer, a mutagenic primer for substituting a Gly codon with an Asn codon by changing two nucleotides (primer P3; SEQ ID NO: 12) and, as reverse primer, a primer containing the 3' end of human RANTES and a sequence later used in cloning step (primer P4; SEQ ID NO: 13).

The resulting products of 138 and 139 bp, which hybridize at level of the common mutated region of RANTES, were purified and mixed at a 1:1 ratio. The solution was diluted 100-fold prior to a second PCR reaction using the original terminal primers (primers P1 and P4). The predicted 244 bp PCR product was purified and digested with BspHI and XhoI restriction endonucleases, cloned into pET24d between NcoI and XhoI sites and transformed into TG1 competent *E. coli* cells. DNA sequence analysis of the resulting vector revealed the expected mutation site (FIG. 1).

The same approach has been used for generating vectors for the expression of the alternative mutants in the same position RANTES G32P (SEQ ID NO: 2), RANTES G32D (SEQ ID NO: 3), and RANTES G32K (SEQ ID NO: 4).

The pET24d-based plasmids encoding for RANTES and the mutants in position 32 were transferred in BL21 (DE3) pLysS competent *E. coli* cells, wherein protein expression was induced by addition of 1 mM isopropyl-β-D-thiogalactopyranoside (IPTG) to the culture. Cells were harvested 3.5 hours after induction and resuspended in lysis buffer (50 mM Tris/HCl pH 8, 10 mM $MgCl_2$, 5 mM Benzamidine/HCl, 1 mM DTT, 0.1 mM phenylmethylsulfonyl fluoride (PMSF), DNase 20 mg/L). Cells were broken by three passages through the French Pressure Cell unit. The suspension was subsequently centrifuged at 10,000×g for 30 minutes at 4° C. The inclusion body pellet containing RANTES or the mutein was solubilised in 0.1 M Tris/HCl, pH 8.0, containing 6M Guanidine/HCl, and 1 mM DTT and stirred for 30 min at 60° C. The solution was dialysed against 3 changes of 1% acetic acid. Insoluble material was removed by centrifugation at 10,000×g for 30 minutes. The supernatant containing the recombinant protein was lyophilized.

The lyophilized powder was dissolved in 0.1 M Tris/HCl, pH 8.0, containing 6M Guanidine/HCl, and 1 mM DTT to obtain a concentration of approximately 1 mg/ml. The proteins were renatured by dropwise dilution into a volume 10 times that of the guanidine solution of 20 mM Tris/HCl, pH 8.0 containing 0.01 mM oxidised glutathione and 0.1 mM reduced glutathione. The solution was stirred overnight at 4° C. Insoluble material was removed by centrifugation 10,000×g for 30 minutes. The pH was adjusted to 4.5 with acetic acid, and the conductivity adjusted to 20 mS by dilution with $H_2O$. The solution was applied to a HiLoad S 26/10 column previously equilibrated in 20 mM sodium acetate, pH 4.5, and protein was eluted with a linear 0-2M NaCl gradient in the same buffer. The fractions containing the recombinant proteins were pooled, dialysed against 3 changes of acetic acid, and lyophilised.

The lyophilised proteins were dissolved in 50 mM Tris/HCl buffer, pH 8.0. The MKKKWPR leader sequence was cleaved from RANTES or the RANTES mutant by incubating with Trypsin (1:10,000, enzyme: substrate, w/w) for 3 hours at 37° C. The cleaved proteins were separated from uncleaved protein by cation exchange chromatography on a HiLoad SP 26/10 column previously equilibrated in 20 mM sodium acetate, pH 4.5, containing 6 M urea, and proteins were eluted with a linear 0-2M NaCl gradient in the same buffer. The cleaved fractions were pooled and dialysed against two changes of 1% acetic acid, and finally against 0.1% trifluoroacetic acid, and then lyophilized before further use.

The identity of all proteins so expressed was verified by mass spectrometry, and the purity by High Pressure Liquid Chromatography (HPLC). The purified, recombinant proteins were analyzed by mass spectrometry to ascertain the correct structure. RANTES had a mass of 7846.69 Da, compared to the expected mass of 7947.04 Da for the oxidised protein. RANTES G32N had a mass of 7904.08 Da, compared to the expected mass of 7903.54 Da for the oxidised protein.

Example 2

Equilibrium Competition Receptor Binding Assays

The assays were carried out on membranes from CHO transfectants expressing CCR1 and CCR5 using a Scintillation Proximity assay (SPA) using $[^{125}I]$-MIP-1α as tracer. Competitors were prepared by serial dilutions of the unlabelled chemokines in binding buffer to cover the range $10^{-6}$-$10^{-12}$ M. The binding buffer used was 50 mM HEPES, pH 7.2 containing 1 mM $CaCl_2$, 5 mM $MgCl_2$, 0.15 M NaCl and 0.5% Bovine Serum Albumin. Wheat germ SPA beads (Amersham) were solubilised in PBS to 50 mg/ml, and diluted in the binding buffer to a 10 mg/ml, and the final concentration in the assay was 0.25 mg/well. Membranes expressing CCR1 or CCR5 were stored at −80° C. and diluted in the binding buffer to a concentration of 80 μg/ml. Equal volumes of membrane and bead stocks were mixed before performing the assay to reduce background. The final membrane concentration was 2 μg/ml and that of $[^{125}I]$-MIP-1α was 0.1 nM. The plates were incubated at room temperature with agitation for 4 hours. Radioactivity was counted (1 min/well) in a beta counter. Data from triplicate samples were analysed using Prism® software (GraphPad).

Figure 2B:
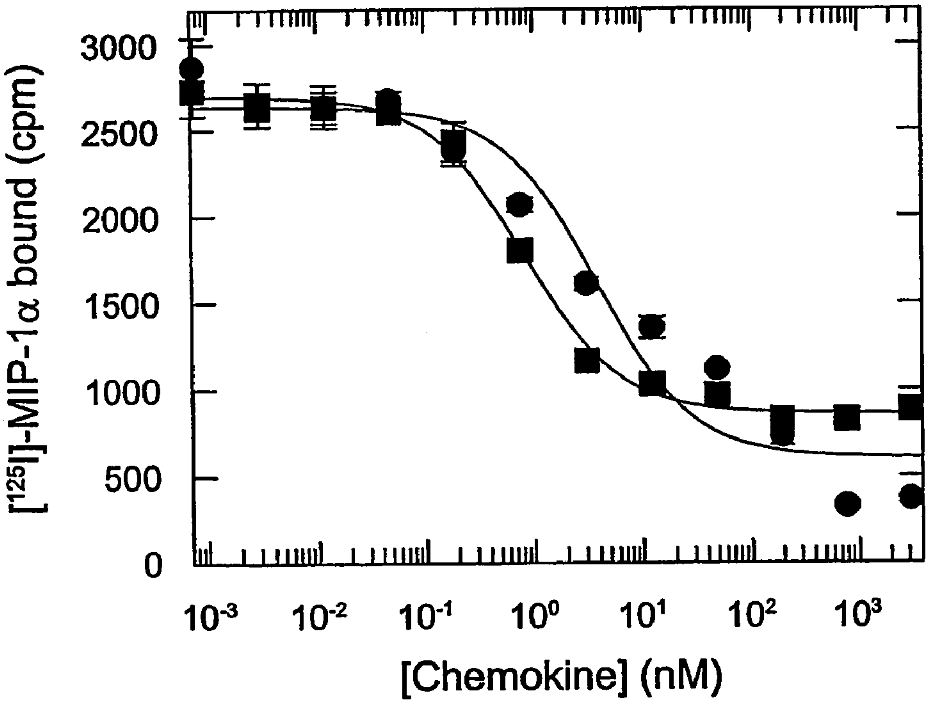

All the RANTES mutants in position 32 retained high affinity binding to both RANTES receptors, CCR1 and CCR5. They were able to compete $[^{125}I]$-MIP-1α for CCR1 (FIG. 2*a*) and CCR5 (FIG. 2*b*) still in the nanomolar range.

Example 3

In Vitro Chemotaxis

Monocytes were purified from buffy coats using the following isolation procedure. A buffy coat solution (100 ml) was diluted with 100 ml PBS, layered on Ficoll and centrifuged at 600×g for 20 min at room temperature. The cells forming the interface were collected and washed twice with PBS. The monocytes were enriched by negative selection by depletion of T cells, NK cells, B cells, dendritic cells and basophils using the MACS cell isolation kit (Miltenyi Biotech).

The monocytes were resuspended at $1.5\times10^6$/ml in RPMI 1640 medium, without Phenol red. The purity was measured by forward and side scatter by FACS analysis. Chemokine dilutions (30 µl), covering the range of $10^{-6}$-$10^{-12}$ M in RPMI medium (without Phenol red), was placed in the lower wells of a 96-well chemotaxis chamber (Neuroprobe). The filter unit (3 µm pore size) was placed over the lower wells ensuring that there are no air bubbles. The cell suspension (20 µl at $1.5\times10^6$ cells/ml in RPMI medium) was placed in the upper wells. The chamber was incubated for 2 h at 37° C. under $O_2$. The upper surface of the filter was washed with 10 mls PBS, and the filter then removed. The migrated cells in the lower chambers were transferred to a second black 96 well plate according to the manufacture's instructions and frozen at −80° C. The plate was then to reach room temperature, and the number of cells enumerated using the CyQUANT cell proliferation assay kit (Molecular Probes) according to the manufacture's instructions. Fluorescence was measured by excitation at 480 nm, and emission at 520 nm, and the data were analyzed using Prism® software (GraphPad).

Figure 3A:
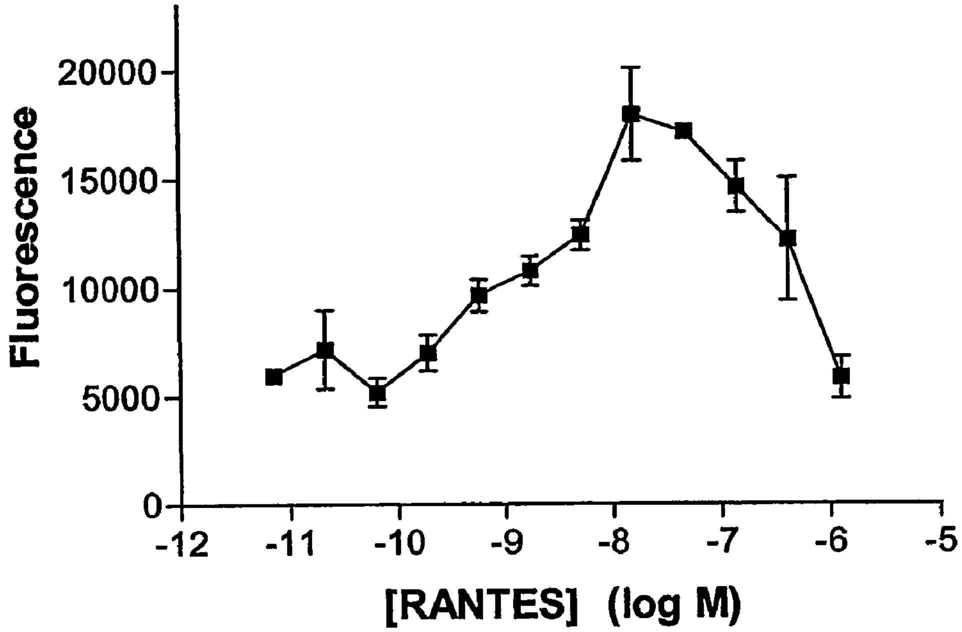
FIG. 3: monocyte chemotaxis induced by RANTES (a) and RANTES G32N (b).
Figure 3B:
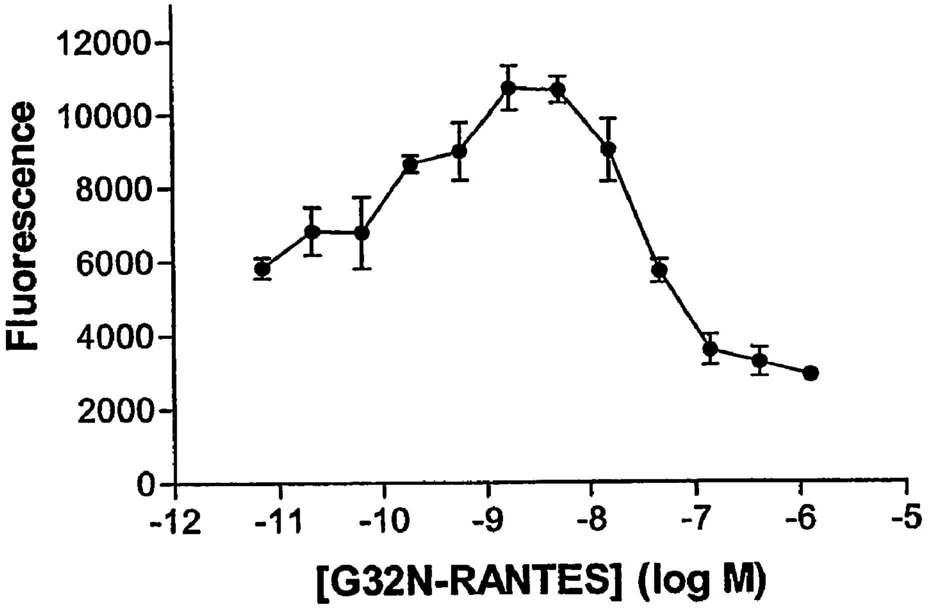

The results obtained in the monocyte chemotaxis assays correlate with the fact that the mutant retains high affinity receptor binding. RANTES G32N was able to induce monocyte chemotaxis with activities comparable to RANTES (FIG. 3). Other evidences on the similarity of the in vitro properties of RANTES mutants have been obtained also in a heparin-binding assay.

Example 4

Peritoneal Cellular Recruitment Assay

Female Balb/C mice of 8 to 12 weeks of age were sensitised on day 0. All mice received 5 sub-cutaneous injections (4×50 µl into each limb and 1×100 µl into the scruff of the neck) of 10 nM CpG-ODN (Microsynth) mixed with 100 µg Ovalbumin (Sigma, Grade V) in sterile PBS.

After a week, cellular recruitment was induced into the Balb/C mice by intraperitoneal injection of 10 µg (0.5 mg/Kg) of RANTES or RANTES G32N mutant diluted in 0.2 ml sterile, lipopolysaccharide-free saline solution (0.9%). When the agonistic properties of RANTES G32N mutant were tested, the indicated amounts of the protein, diluted in 0.2 ml of the same sterile solution, were administered 30 minutes prior to the agonist (RANTES) administration.

Mice were sacrificed by aerosolized $CO_2$ 16 hours later, and peritoneal lavage was performed with 5 ml PBS three times. The lavages were pooled and centrifuged at 1500×g for 5 minutes, and the pelleted cells were resuspended in a final volume of 1 milliliter. The total number of elicited leukocytes for each sample was counted with a hemacytometer.

Figure 4:
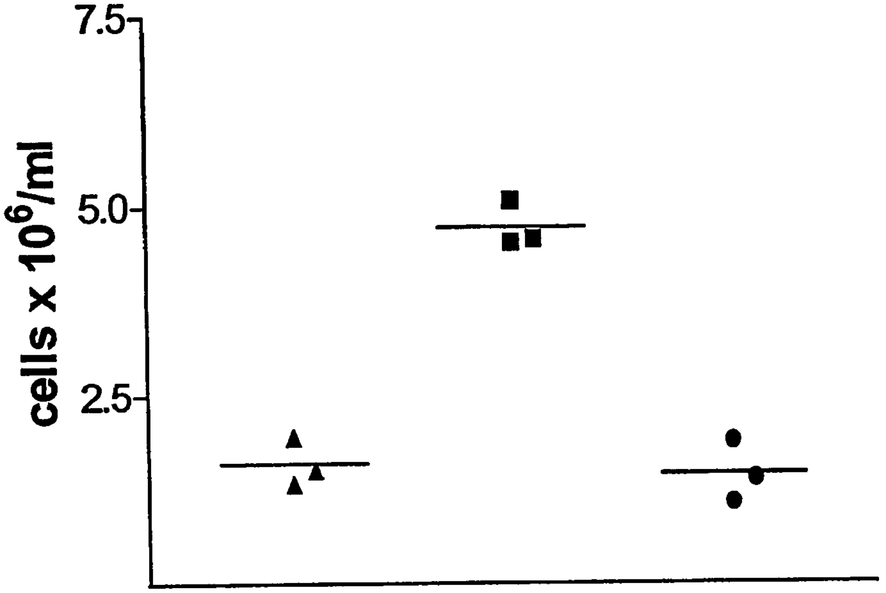
FIG. 4: induction of cellular recruitment into the peritoneum by 10 μg RANTES (■) and 10 μg RANTES G32N (●) compared to the basal level observed with the administration of saline solution (▲).
Figure 5:
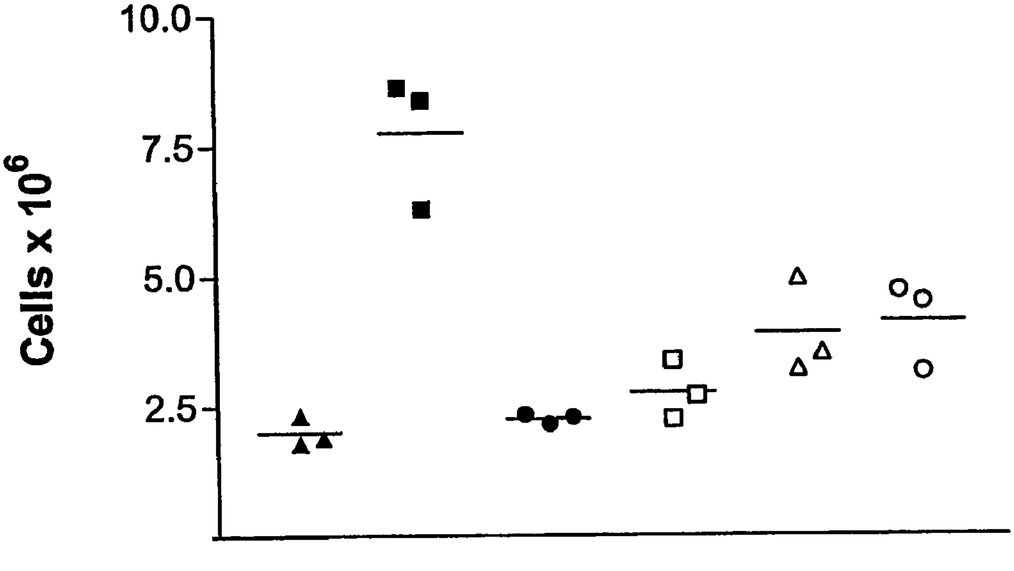
FIG. 5: inhibition of the RANTES induced peritoneal recruitment by RANTES G32N. Inhibition of the peritoneal cellular recruitment induced by 10 μg RANTES (■) was determined by the administration of 10 μg RANTES G32N (□), 1 μg RANTES G32N (Δ) and 0.1 μg RANTES G32N (○) 30 minutes prior to the RANTES administration compared to the basal recruitment observed by administration of saline solution alone (▲). A treatment with 1 μg Met-RANTES was used as a positive control for inhibition (●).

RANTES G32N mutant was not able to induce cellular recruitment into the peritoneum at the dose (10 µg/mouse) that RANTES causes substantial recruitment (FIG. 4). On the other side, when the mutant is administered 30 minutes prior to the administration of RANTES, the cellular recruitment induced by RANTES is inhibited in a dose related manner by RANTES G32N, with an statistically significant efficacy similar to the known RANTES antagonist Met-RANTES (FIG. 5).

Example 5

Ovalbumin Induced Lung Inflammation Assay

Ovalbumin sensitized mice, when challenged intra-nasally with ovalbumin, develop symptoms that resemble those of human asthma. The inflammatory response is associated with a large infiltrate of leukocytes into the lungs, and this can be measured by brochoalveolar lavage.

Female Balb/c mice aged between 8-12 weeks (n=6 per group) were injected intra peritoneally (i.p.) with 10 µg Ovalbumin (Sigma A-5503) plus 2% $AlOH_3$ in 200 µl NaCl. The sham group were injected with saline solution alone.

On days 15-19 inclusive, mice were injected i.p. with 10 µg RANTES G32N or 1 µg Met-RANTES in 200 µl sterile saline solution as a positive control, or 200 µl saline solution (NaCl) as a negative control, 30 minutes prior to intra nasal administration of 15 µg Ovalbumin in 50 µl saline solution under inhalational anaesthesia. Mice were sacrificed on day 22 with an overdose of Urethane i.p., and lungs were lavaged with 4×0.4 ml ice cold PBS-EDTA. Total cells recovered from each animal were enumerated manually with a haemocytometer.

Figure 6:
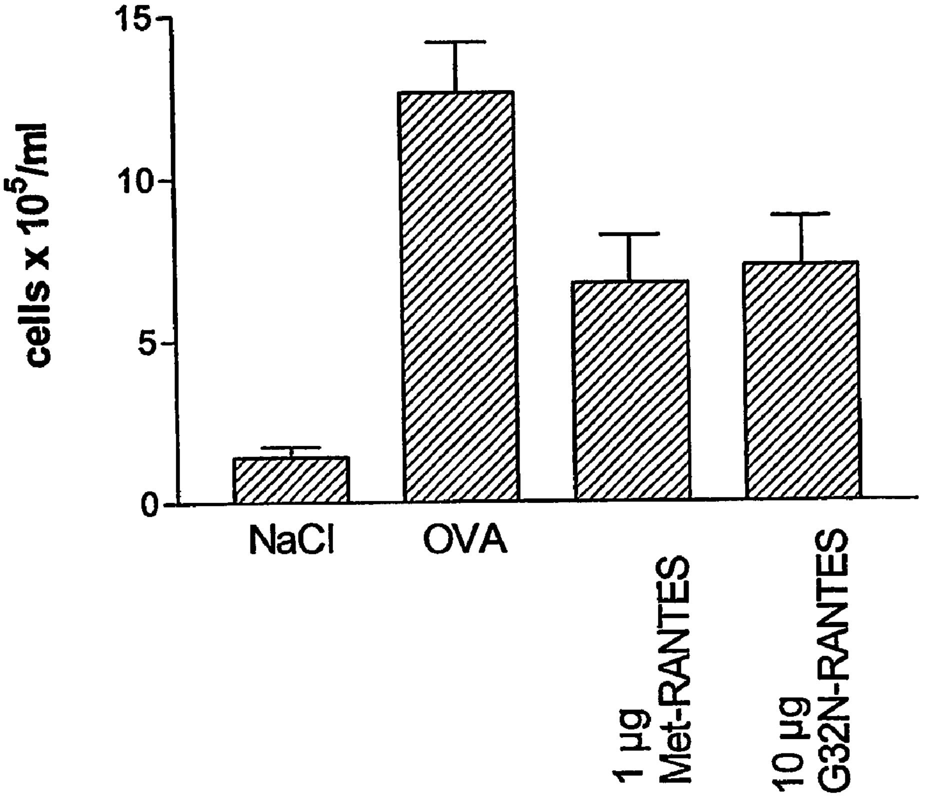
FIG. 6: effect of RANTES G32N in preventing cellular recruitment into the airways of ovalbumin sensitized mice. The mice were either not sensitized with ovalbumin but simply with saline solution, which is the negative control (NaCl), or were sensitized with ovalbumin but treated with saline solution to give the positive control group (OVA). The Met-RANTES treatment was used as a control for inhibition.

RANTES G32N (10 µg/mouse) was able to inhibit the cellular recruitment by 48% compared to 52% observed with a 1 µg/mouse of Met-RANTES, the positive control for the treatment (FIG. 6).

Example 6

Delayed Contact Hypersensitivity Assay

Contact hypersensitivity responses (CHS) are hapten-specific skin inflammations mediated by T cells. Most haptens give rise to an oligoclonal T-cell response consisting mainly of $CD8^+$ effector T cells, whereas $CD4^+$ T cells have a down-regulatory role in the CHS response.

The mouse ear-swelling test to measure contact hypersensitivity was performed as described (Garrigue J L et al., 1994). Briefly, mice were pre-sensitized topically by applying 25 µl of 0.5% 2,4-dinitrofluorobenzene (DNFB; Sigma Chemical Co.) solution in acetone/olive oil (4:1) to the shaved abdomen. Five days later, 20 µl of 0.2% DNFB in the same vehicle was applied to the right ears, and vehicle alone to the left ears, in order to induce a chemotaxis of cells inducing ear swelling.

Treatments were started at the time of challenge and administered daily as an intraperitoneal injection. The delta in ear swelling was calculated as the change in the size of the left ear as compared to the right ear of the same mouse on days 5-12 post sensitization. Mice were treated daily from Day 5 to 9 with an intraperitoneal administration of 0.5 mg/kg RANTES G32N, or 12.5 mg/kg IL-18 binding protein. The first treatment was administered 1 hour prior to the DNFB challenge. Ear thickness was measured with a dial thickness gauge (Mitutoyo Corp.), and ear swelling was estimated by subtracting the pre-challenge from the post-challenge value, and by further subtracting any swelling detected in the vehicle-challenged contralateral ear.

Figure 7:
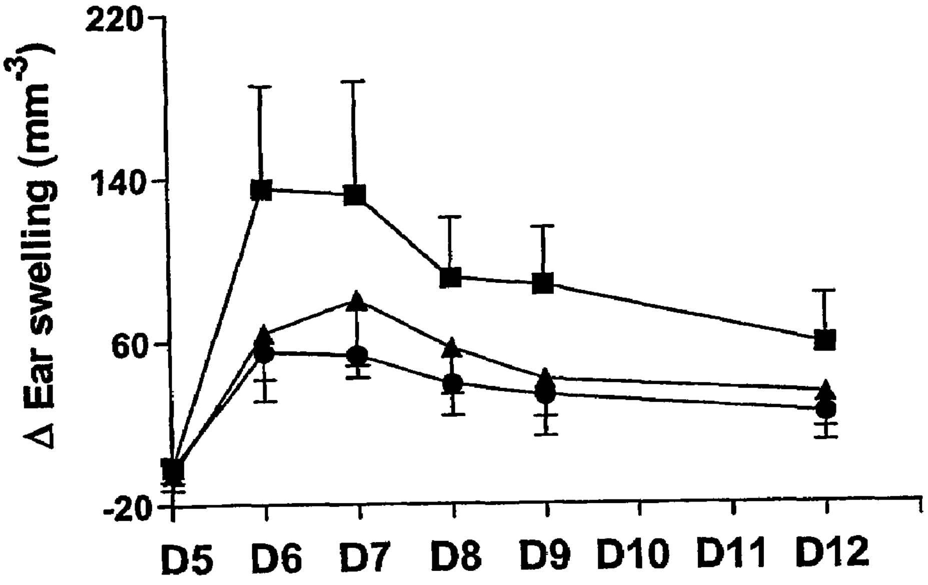
FIG. 7: inhibition of contact hypersensitivity. The treatment groups included 0.5 mg/kg RANTES G32N (●) and 12.5 mg/kg IL-18 binding protein (reference control; ▲), to be compared with PBS (negative control; ■). Ear swelling were measured at days 0, 5, 6, 7, 8, 9, 12, 14, 16. Student T test was used to determine significant differences for vehicle versus RANTES G32N: D6 p=0.0117; D7 p=0.0146; D8 p=0.0083; D9 p=0.0107; D12 p=0.0334.

DNFB challenge at day 5 induced significant ear swelling in both treatment groups when compared to vehicle control (FIG. 7), going back to almost normal state already at day 9. In this established murine model of contact hypersensitivity/contact dermatitis, a three day treatment with a CC-chemokine mutant of the invention had a significant beneficial effect on the extent of swelling/inflammation elicited by treatment with a hapten.

Example 7

Crystallographic Structure of RANTES G32N and Other CC-Chemokines Mutants Having Antagonistic Properties In order to determine the crystallographic structure of RANTES G32N, therecombinant protein was dissolved at 10 mg/ml in water, and the pH adjusted to 3.5 by the addition of 50 mM Acetate buffer pH 3.5. Crystals were grown by the hanging-drop vapor diffusion method in which 5 μl of the protein solution were mixed with 51 μl of the reservoir solution and equilibrated against 1 ml of reservoir solution. This solution was composed of 15-20% (v/v) polyethylene glycol (PEG) 400, 100 mM Acetate buffer pH 4.5 and 10% (v/v) glycerol. Crystals were soaked in a cryoprotectant solution composed of 25% (v/v) PEG 400, 100 mM Acetate buffer pH 4.5 and 10% (v/v) glycerol and frozen directly in nitrogen stream at −190° C. Crystallographic data was collected at −190° C. on a MAR345 x-ray detector coupled to a Siemens XG-12 rotating anode generator, and the data processed with DENZO and SCALEPACK software.

Figure 8:
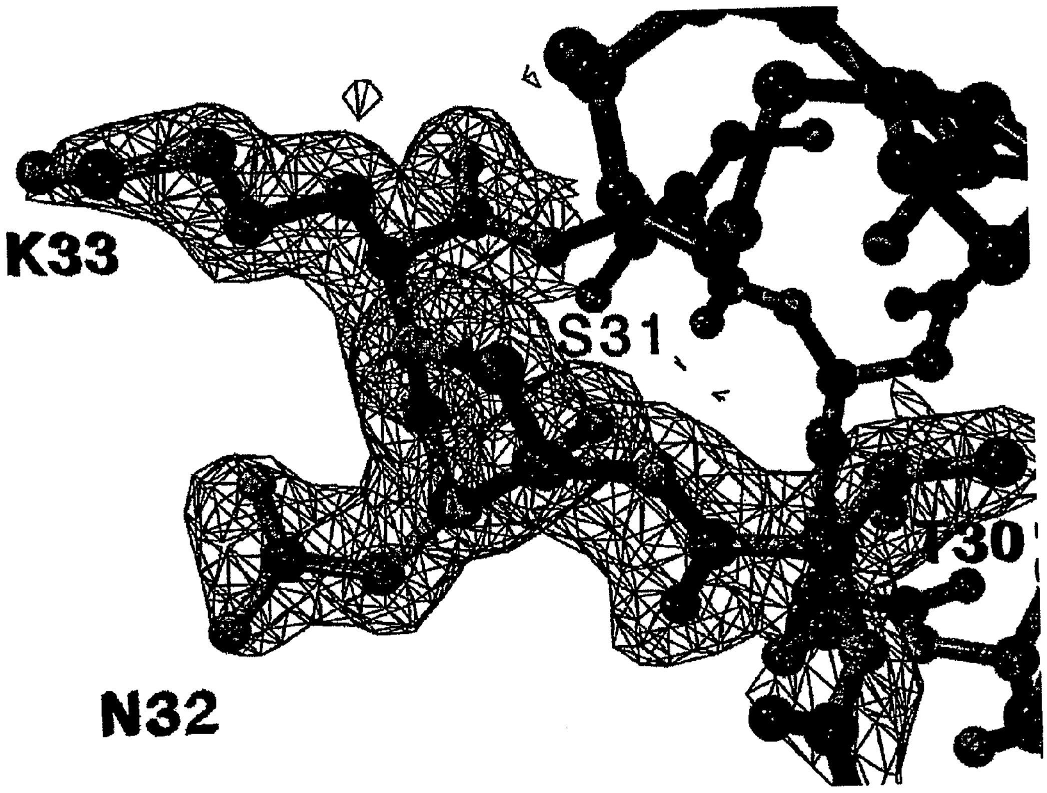
FIG. 8: structure of RANTES G32N, showing 2fo-fc electron density contoured at 2σ around residues Thr30-Ser31-Gly32-Lys33, and in particular the mutation of Gly 32 to Asn.

The protein crystallized in the same spacegroup as RANTES wild type and with similar unit cell dimensions. Examination of the fo-fc electron density map revealed the presence of new electron density at the Gly32, confirming the mutation to Asn (FIG. 8).

The analysis of the structure of RANTES G32N and comparison with the sequence and the structure of other known CC-chemokines (FIGS. 1 and 9) suggests that the substituted residue may play a general role in CC-chemokine biological activity. This specific position 32, together with Thr30 and Ser31 and the surrounding conserved Cys residues, defines a consensus sequence common to a subset of CC-chemokines for which it can inferred that a similar non-conservative substitution can lead to a mutant having antagonistic properties.

TABLE I

| Amino Acid | Synonymous Group | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |

TABLE II-continued

| Amino Acid | Synonymous Group |
|---|---|
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S—Me—Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S—Me—Cys, Ile, D-Ile, Leu, D-Leu, Val, D-Val |

REFERENCES

Appay V and Rowland-Jones S L, Trends Immunol, 22: 83-7, 2001.

Baggiolini M et al., Annu Rev Immunol, 15: 675-705, 1997.

Baggiolini M, J Intern Med, 250: 91-104, 2001.

Beck C et al., J Biol Chem, 276: 43270-6, 2001.

Brown A et al., J Pept Sci, 2: 40-6, 1996.

Cleland J L et al., Curr Opin Biotechnol, 12: 212-9, 2001.

Dougherty D A, Curr Opin Chem Bio, 4: 645-52, 2000.

Edgerton M D et al., Methods Mol Biol, 138: 33-40, 2000.

Fernandez E J and Lolis E, Annu Rev Pharmacol Toxicol, 42:469-499, 2002.

Garrigue J L et al., Contact Dermatitis, 30: 231-7, 1994.

Godessart N and Kunkel S L, Curr Opin Immunol, 13: 670-675, 2001.

Golebiowski A et al., Curr Opin Drug Discov Devel, 4: 428-34, 2001.

Gong J and Clark-Lewis I, J Exp Med 181: 631-640, 1995.

Gong J H et al., J Biol Chem, 271: 10521-7, 1996.

Hemmerich S et al., Biochemistry, 38: 13013-13025, 1999.

Hruby V J and Balse P M, Curr Med Chem, 7:945-70, 2000

Luo B and Prestwich G D, Exp Opin Ther Patients, 11: 1395-1410, 2001.

Martin L et al., Biochemistry, 40: 6303-18, 2001

Mayer M R and Stone M J, J Biol Chem, 276: 13911-6, 2001.

Murphy L R et al., Protein Eng, 13:149-52, 2000.

Nardese V et al., Nat Struct Biol, 8: 611-5, 2001.

Pillai O and Panchagnula R, Cur Opin Chem Biol, 5: 447-451, 2001

Proudfoot A et al., Immunol Rev, 177: 246-56, 2000.

Rajarathnam K, Curr Pharm Des, 8: 2159-69, 2002.

Rogov S I and Nekrasov A N, Protein Eng, 14: 459-463, 2001.

Rossi D and Zlotnik A, Annu Rev Immunol, 18:217-42 2000

Sawyer T K, in "Structure Based Drug Design", edited by Veerapandian P, Marcel Dekker Inc., pg. 557-663, 1997.

Schneider G P et al., Int J Mol Med, 8: 235-44, 2001.

Villain M et al., Chem Biol, 8 (7):673-9, 2001.

Vita C et al., J Immunol Methods, 266: 53-65, 2002.

The invention claimed is:

1. An isolated mutant of CCL5 (RANTES) comprising SEQ ID NO: 1, 4, 5, 6 or 7, wherein said mutant antagonizes in vivo cellular recruitment caused by CCL5.

2. An isolated polypeptide comprising a heterologous polypeptide sequence and a polypeptide selected from the group consisting of SEQ ID NO: 1, 4, 5, 6 and 7.

3. The polypeptide according to claim 2, wherein said heterologous polypeptide sequence comprises an amino acid sequence selected from one or more of the following protein sequences: extracellular domains of membrane-bound protein, immunoglobulin constant regions, multimerization domains, extracellular proteins, signal peptide-containing proteins, or export signal-containing proteins.

4. A pharmaceutical composition comprising a pharmaceutically acceptable excipient and a mutant of CCL5 (RANTES) comprising SEQ ID NO: 1, 4, 5, 6 or 7, wherein said mutant antagonizes in vivo cellular recruitment caused by CCL5.

5. A method of making a pharmaceutical composition comprising combining a pharmaceutically acceptable excipient and a mutant of CCL5 (RANTES) according to claim 1.

6. The isolated mutant according to claim 1, wherein said mutant comprises SEQ ID NO: 1.

7. The isolated mutant according to claim 1, wherein said mutant comprises SEQ ID NO: 4.

8. The isolated mutant according to claim 1, wherein said mutant comprises SEQ ID NO: 5.

9. The isolated mutant according to claim 1, wherein said mutant comprises SEQ ID NO: 6.

10. The isolated mutant according to claim 1, wherein said mutant comprises SEQ ID NO: 7.

11. The isolated polypeptide according to claim 2, wherein said isolated polypeptide comprises a heterologous polypeptide sequence and SEQ ID NO: 1.

12. The isolated polypeptide according to claim 2, wherein said isolated polypeptide comprises a heterologous polypeptide sequence and SEQ ID NO: 4.

13. The isolated polypeptide according to claim 2, wherein said isolated polypeptide comprises a heterologous polypeptide sequence and SEQ ID NO: 5.

14. The isolated polypeptide according to claim 2, wherein said isolated polypeptide comprises a heterologous polypeptide sequence and SEQ ID NO: 6.

15. The isolated polypeptide according to claim 2, wherein said isolated polypeptide comprises a heterologous polypeptide sequence and SEQ ID NO: 7.

16. The pharmaceutical composition according to claim 4, wherein said mutant comprises SEQ ID NO: 1.

17. The pharmaceutical composition according to claim 4, wherein said mutant comprises SEQ ID NO: 4.

18. The pharmaceutical composition according to claim 4, wherein said mutant comprises SEQ ID NO: 5.

19. The pharmaceutical composition according to claim 4, wherein said mutant comprises SEQ ID NO: 6.

20. The pharmaceutical composition according to claim 4, wherein said mutant comprises SEQ ID NO: 7.

* * * * *

UNITED STATES PATENT AND TRADEMARK OFFICE

CERTIFICATE OF CORRECTION

PATENT NO. : 7,553,483 B2 
APPLICATION NO. : 10/499100
DATED : June 30, 2009
INVENTOR(S) : Amanda Proudfoot, Marie Kosco-Vilbois and Jeffrey Shaw It is certified that error appears in the above-identified patent and that said Letters Patent is hereby corrected as shown below:

Column 4,
Line 44, “exemplified In the” should read --exemplified in the--.

Column 5,
Line 50, “previously Indicated” should read --previously indicated--.

Column 17,
Line 8, “therecombinant protein” should read --the recombinant protein--.

Signed and Sealed this

Twenty-fifth Day of August, 2009

David J. Kappos
*Director of the United States Patent and Trademark Office*